US010478504B2

(12) United States Patent
Guido et al.

(10) Patent No.: US 10,478,504 B2
(45) Date of Patent: Nov. 19, 2019

(54) TAMPER RESISTANT PHARMACEUTICAL FORMULATIONS

(71) Applicant: Purdue Pharma L.P., Stamford, CT (US)

(72) Inventors: Debora Guido, Bordentown, NJ (US); Haiyong Hugh Huang, Princeton Junction, NJ (US)

(73) Assignee: PURDUE PHARMA L.P., Stamford, CT (US)

(*) Notice: Subject to any disclaimer, the term of this patent is extended or adjusted under 35 U.S.C. 154(b) by 0 days.

(21) Appl. No.: 15/588,066

(22) Filed: May 5, 2017

(65) Prior Publication Data

US 2017/0296671 A1    Oct. 19, 2017

Related U.S. Application Data

(63) Continuation of application No. 14/670,662, filed on Mar. 27, 2015, now Pat. No. 9,662,399, which is a continuation of application No. 14/172,447, filed on Feb. 4, 2014, now Pat. No. 9,149,533.

(60) Provisional application No. 61/761,055, filed on Feb. 5, 2013.

(51) Int. Cl.
| | |
|---|---|
| A61K 9/20 | (2006.01) |
| A61K 9/24 | (2006.01) |
| A61K 31/74 | (2006.01) |
| A61K 31/78 | (2006.01) |
| A61K 47/02 | (2006.01) |
| A61K 47/32 | (2006.01) |
| A61K 47/36 | (2006.01) |
| A61K 31/165 | (2006.01) |
| A61K 31/167 | (2006.01) |
| A61K 31/485 | (2006.01) |
| A61K 31/715 | (2006.01) |
| A61K 31/717 | (2006.01) |
| A61K 31/5375 | (2006.01) |

(52) U.S. Cl.
CPC .............. *A61K 47/36* (2013.01); *A61K 9/205* (2013.01); *A61K 9/2009* (2013.01); *A61K 9/2013* (2013.01); *A61K 9/2027* (2013.01); *A61K 9/2031* (2013.01); *A61K 31/165* (2013.01); *A61K 31/167* (2013.01); *A61K 31/485* (2013.01); *A61K 47/02* (2013.01); *A61K 47/32* (2013.01); *A61K 9/209* (2013.01); *A61K 31/5375* (2013.01); *A61K 31/715* (2013.01); *A61K 31/717* (2013.01); *A61K 31/74* (2013.01); *A61K 31/78* (2013.01)

(58) Field of Classification Search
CPC .............. A61K 31/5375; A61K 31/715; A61K 31/717; A61K 31/74; A61K 31/78; A61K 31/485

USPC ......................... 514/472, 282, 812
See application file for complete search history.

(56) References Cited

U.S. PATENT DOCUMENTS

| | | | |
|---|---|---|---|
| 3,065,143 A | 11/1962 | Christenson et al. | |
| 3,133,132 A | 5/1964 | Loeb et al. | |
| 3,173,876 A | 3/1965 | Zobrist et al. | |
| 3,260,646 A | 7/1966 | Paulsen et al. | |
| 3,276,586 A | 10/1966 | Rosaen | |
| 3,541,005 A | 11/1970 | Strathmann et al. | |
| 3,541,006 A | 11/1970 | Bixler et al. | |
| 3,546,876 A | 12/1970 | Fokker et al. | |
| 3,845,770 A | 11/1974 | Theeuwes et al. | |
| 3,916,889 A | 11/1975 | Russell | |
| 3,965,256 A | 6/1976 | Leslie | |
| 3,980,766 A | 9/1976 | Shaw et al. | |
| 4,063,064 A | 12/1977 | Saunders et al. | |
| 4,070,494 A | 1/1978 | Hollmelster et al. | |
| 4,088,864 A | 5/1978 | Theeuwes et al. | |
| 4,160,020 A | 7/1979 | Ayer et al. | |
| 4,175,119 A | 11/1979 | Porter | |
| 4,200,098 A | 4/1980 | Ayer et al. | |
| 4,235,870 A | 11/1980 | Leslie | |
| 4,285,987 A | 8/1981 | Ayer et al. | |
| 4,293,539 A | 10/1981 | Ludwig et al. | |
| 4,366,310 A | 12/1982 | Leslie | |
| 4,385,057 A | 5/1983 | Bjork et al. | |
| 4,389,393 A | 6/1983 | Schor et al. | |
| 4,424,205 A | 1/1984 | LaHann et al. | |
| 4,443,428 A | 4/1984 | Oshlack et al. | |
| 4,457,933 A | 7/1984 | Gordon et al. | |
| 4,459,278 A | 7/1984 | Porter | |
| 4,588,580 A | 5/1986 | Gale et al. | |
| 4,599,342 A | 7/1986 | LaHann | |
| 4,610,870 A | 9/1986 | Jain et al. | |
| 4,612,008 A | 9/1986 | Wong et al. | |
| 4,666,705 A | 5/1987 | DeCrosta et al. | |
| 4,764,378 A | 8/1988 | Keith et al. | |
| 4,765,989 A | 8/1988 | Wong et al. | |

(Continued)

FOREIGN PATENT DOCUMENTS

| | | |
|---|---|---|
| CA | 2569743 | 12/2005 |
| CA | 2 746 888 | 6/2010 |

(Continued)

OTHER PUBLICATIONS

The United States Pharmacopeial Convention, 711 Dissolution, pp. 1-8 (Dec. 2011).*
Supplemental European Search Report for 147491815-1466/2953618 dated Oct. 31, 2016, 9pgs.
Ortho-McNeil-Janssen Pharmaceuticals, Inc. (2010). Prescribing Information for Concerta Extended-Release Tablets.
International Search Report for International Application No. PCT/US14/14665 filed on Feb. 4, 2014, dated May 5, 2014, 10 pgs.

(Continued)

*Primary Examiner* — Kevin E Weddington
(74) *Attorney, Agent, or Firm* — Lowenstein Sandler LLP

(57) ABSTRACT

Disclosed in certain embodiments is a solid oral dosage form comprising a heat-labile gelling agent; a thermal stabilizer; and a drug susceptible to abuse.

14 Claims, No Drawings

(56) References Cited

U.S. PATENT DOCUMENTS

| | | |
|---|---|---|
| 4,769,372 A | 9/1988 | Kreek |
| 4,785,000 A | 11/1988 | Kreek et al. |
| 4,806,341 A | 2/1989 | Chien et al. |
| 4,812,446 A | 3/1989 | Brand |
| 4,834,984 A | 5/1989 | Goldie et al. |
| 4,844,909 A | 7/1989 | Goldie et al. |
| 4,861,598 A | 8/1989 | Oshlack |
| 4,957,681 A | 9/1990 | Klimesch et al. |
| 4,970,075 A | 11/1990 | Oshlack |
| 4,990,341 A | 2/1991 | Goldie et al. |
| 5,026,556 A | 6/1991 | Drust et al. |
| 5,059,600 A | 10/1991 | Gawin et al. |
| 5,069,909 A | 12/1991 | Sharma et al. |
| 5,111,942 A | 5/1992 | Bernardin |
| 5,114,942 A | 5/1992 | Gawin et al. |
| 5,130,311 A | 7/1992 | Guillaumet et al. |
| 5,149,538 A | 9/1992 | Granger et al. |
| 5,169,645 A | 12/1992 | Shukla et al. |
| 5,202,128 A | 4/1993 | Morella et al. |
| 5,215,758 A | 6/1993 | Krishnamurthy |
| 5,225,199 A | 7/1993 | Hidaka et al. |
| 5,240,711 A | 8/1993 | Hille et al. |
| 5,266,331 A | 11/1993 | Oshlack et al. |
| 5,273,758 A | 12/1993 | Royce |
| 5,273,760 A | 12/1993 | Oshlack et al. |
| 5,286,493 A | 2/1994 | Oshlack et al. |
| 5,290,816 A | 3/1994 | Blumberg |
| 5,321,012 A | 6/1994 | Mayer et al. |
| 5,324,351 A | 6/1994 | Oshlack et al. |
| 5,330,766 A | 7/1994 | Morella et al. |
| 5,356,467 A | 10/1994 | Oshlack et al. |
| 5,376,705 A | 12/1994 | Leys et al. |
| 5,378,474 A | 1/1995 | Morella et al. |
| 5,403,868 A | 4/1995 | Reid et al. |
| 5,409,944 A | 4/1995 | Black et al. |
| 5,411,745 A | 5/1995 | Oshlack et al. |
| 5,422,123 A | 6/1995 | Conte et al. |
| 5,425,950 A | 6/1995 | Dandiker et al. |
| 5,436,265 A | 7/1995 | Black et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,489,439 A | 2/1996 | Bola |
| 5,500,227 A | 3/1996 | Oshlack et al. |
| 5,502,058 A | 3/1996 | Mayer et al. |
| 5,508,042 A | 4/1996 | Oshlack et al. |
| 5,510,368 A | 4/1996 | Lau et al. |
| 5,514,680 A | 5/1996 | Weber et al. |
| 5,521,213 A | 5/1996 | Rasit et al. |
| 5,536,752 A | 7/1996 | Ducharme et al. |
| 5,549,912 A | 8/1996 | Oshlack et al. |
| 5,549,913 A | 8/1996 | Colombo et al. |
| 5,550,142 A | 8/1996 | Ducharme et al. |
| 5,552,422 A | 9/1996 | Gauthier et al. |
| 5,556,838 A | 9/1996 | Mayer et al. |
| 5,580,578 A | 12/1996 | Oshlack et al. |
| 5,593,694 A | 1/1997 | Hayashida et al. |
| 5,593,695 A | 1/1997 | Merrill et al. |
| 5,593,994 A | 1/1997 | Batt et al. |
| 5,604,253 A | 2/1997 | Lau et al. |
| 5,604,260 A | 2/1997 | Guay et al. |
| 5,616,601 A | 4/1997 | Khanna et al. |
| 5,639,476 A | 6/1997 | Oshlack et al. |
| 5,639,780 A | 6/1997 | Lau et al. |
| 5,654,005 A | 8/1997 | Chen et al. |
| 5,656,295 A | 8/1997 | Oshlack et al. |
| 5,667,805 A | 9/1997 | Merrill et al. |
| 5,672,360 A | 9/1997 | Sadder et al. |
| 5,676,972 A | 10/1997 | Galiatsatos et al. |
| 5,679,650 A | 10/1997 | Ukunaga et al. |
| 5,681,585 A | 10/1997 | Oshlack et al. |
| 5,695,781 A | 12/1997 | Zhang et al. |
| 5,741,524 A | 4/1998 | Staniforth et al. |
| 5,762,963 A | 6/1998 | Byas-Smith |
| 5,788,987 A | 8/1998 | Busetti et al. |
| 5,811,388 A | 9/1998 | Friend et al. |
| 5,814,336 A | 9/1998 | Kelm et al. |
| 5,837,379 A | 11/1998 | Chen et al. |
| 5,843,480 A | 12/1998 | Miller et al. |
| 5,849,240 A | 12/1998 | Miller et al. |
| 5,866,164 A | 2/1999 | Kuczynski et al. |
| 5,879,705 A | 3/1999 | Heafield et al. |
| 5,891,471 A | 4/1999 | Miller et al. |
| 5,891,919 A | 4/1999 | Blum et al. |
| 5,914,131 A | 6/1999 | Miller et al. |
| 5,958,452 A | 9/1999 | Oshlack et al. |
| 5,958,459 A | 9/1999 | Chasin et al. |
| 5,965,161 A | 10/1999 | Oshlack et al. |
| 5,965,163 A | 10/1999 | Miller et al. |
| 5,968,551 A | 10/1999 | Oshlack et al. |
| 6,024,982 A | 2/2000 | Oshlack et al. |
| 6,143,322 A | 11/2000 | Sackler et al. |
| 6,153,621 A | 11/2000 | Hamann |
| 6,162,467 A | 12/2000 | Miller et al. |
| 6,228,863 B1 | 5/2001 | Palermo et al. |
| 6,245,357 B1 | 6/2001 | Edgren et al. |
| 6,277,398 B1 | 8/2001 | Caruso |
| 6,294,194 B1 | 9/2001 | Horhota et al. |
| 6,309,668 B1 | 10/2001 | Bastin et al. |
| 6,352,721 B1 | 3/2002 | Faour |
| 6,365,185 B1 | 4/2002 | Ritschel et al. |
| 6,372,254 B1 | 4/2002 | Ting et al. |
| 6,375,957 B1 | 4/2002 | Kaiko et al. |
| 6,419,954 B1 | 7/2002 | Chu |
| 6,440,464 B1 | 8/2002 | Hsla et al. |
| 6,455,537 B1 | 9/2002 | Cooper |
| 6,485,748 B1 | 11/2002 | Chen et al. |
| 6,488,963 B1 | 12/2002 | McGinity |
| 6,491,949 B2 | 12/2002 | Faour et al. |
| 6,559,159 B2 | 5/2003 | Carroll et al. |
| 6,572,885 B2 | 6/2003 | Oshlack et al. |
| 6,593,367 B1 | 7/2003 | Dewey et al. |
| 6,627,635 B2 | 9/2003 | Palermo et al. |
| 6,696,088 B2 | 2/2004 | Oshlack et al. |
| 6,723,340 B2 | 4/2004 | Gusler et al. |
| 6,730,321 B2 | 5/2004 | Ting et al. |
| 6,733,783 B2 | 5/2004 | Oshlack et al. |
| 6,761,895 B2 | 7/2004 | Sawada et al. |
| 6,955,821 B2 | 10/2005 | Davis et al. |
| 6,987,082 B2 | 1/2006 | Tijsma et al. |
| RE39,239 E | 8/2006 | Busetti et al. |
| 7,201,913 B1 | 4/2007 | Muggetti et al. |
| 7,201,920 B2 | 4/2007 | Kumar et al. |
| 7,399,488 B2 | 7/2008 | Hirsch et al. |
| 7,718,194 B2 | 5/2010 | Chenevier et al. |
| 7,776,314 B2 | 8/2010 | Bartholomaus |
| 7,842,307 B2 * | 11/2010 | Oshlack ............... A61K 9/1635 424/450 |
| 7,943,174 B2 | 5/2011 | Oshlack et al. |
| 8,053,438 B2 | 11/2011 | Allen et al. |
| 8,075,872 B2 | 12/2011 | Arkenau-Maric |
| 8,101,630 B2 | 1/2012 | Kumar et al. |
| 8,114,383 B2 | 2/2012 | Barthalomaus |
| 8,114,384 B2 | 2/2012 | Arkenau |
| 8,143,267 B2 | 3/2012 | Burch et al. |
| 8,153,821 B2 | 4/2012 | Akireddy et al. |
| 8,192,722 B2 | 6/2012 | Arkenau-Maric |
| 8,193,209 B2 | 6/2012 | Burch et al. |
| 8,293,277 B2 | 10/2012 | Swanson et al. |
| 8,309,060 B2 | 11/2012 | Bartholomaus et al. |
| 8,323,692 B2 | 12/2012 | Frisbee |
| 8,329,212 B2 | 12/2012 | Anderson et al. |
| 8,337,888 B2 | 12/2012 | Wright et al. |
| 8,394,408 B2 | 3/2013 | Han et al. |
| 8,551,520 B2 | 10/2013 | Oshlack et al. |
| 8,609,143 B2 | 12/2013 | Fischer et al. |
| 8,617,600 B2 | 12/2013 | Bhatt et al. |
| 8,647,667 B2 | 2/2014 | Oshlack et al. |
| 8,652,529 B2 | 2/2014 | Guimberteau et al. |
| 8,808,740 B2 | 8/2014 | Huang |
| 9,149,533 B2 * | 10/2015 | Guido .................. A61K 9/205 |
| 9,545,448 B2 | 1/2017 | Guido et al. |
| 9,579,389 B2 | 2/2017 | Guido et al. |

(56) References Cited

U.S. PATENT DOCUMENTS

| | | |
|---|---|---|
| 9,655,971 B2 | 5/2017 | Guido et al. |
| 9,662,399 B2 * | 5/2017 | Guido .................. A61K 9/205 |
| 2002/0028240 A1 | 3/2002 | Sawada et al. |
| 2003/0004177 A1 | 1/2003 | Kao et al. |
| 2003/0026838 A1 | 2/2003 | Farrell |
| 2003/0035839 A1 | 2/2003 | Hirsh et al. |
| 2003/0059471 A1 | 3/2003 | Compton et al. |
| 2003/0064099 A1 | 4/2003 | Oshlack et al. |
| 2003/0064122 A1 | 4/2003 | Goldberg et al. |
| 2003/0068276 A1 | 4/2003 | Hughes et al. |
| 2003/0068370 A1 | 4/2003 | Sackler |
| 2003/0068375 A1 | 4/2003 | Wright et al. |
| 2003/0068392 A1 | 4/2003 | Sackler |
| 2003/0082230 A1 | 5/2003 | Baichwal et al. |
| 2003/0091625 A1 | 5/2003 | Hariharan et al. |
| 2003/0124061 A1 | 7/2003 | Roberts |
| 2003/0124185 A1 | 7/2003 | Oshlack et al. |
| 2003/0125347 A1 | 7/2003 | Anderson et al. |
| 2003/0126428 A1 | 7/2003 | Liu et al. |
| 2003/0170181 A1 | 9/2003 | Midha |
| 2003/0206954 A1 | 11/2003 | Lerner et al. |
| 2003/0232081 A1 | 12/2003 | Doshi et al. |
| 2004/0047907 A1 | 3/2004 | Oshlack et al. |
| 2004/0126428 A1 | 7/2004 | Hughes et al. |
| 2004/0131552 A1 | 7/2004 | Oehm |
| 2004/0151791 A1 | 8/2004 | Mayo-Alvarez et al. |
| 2004/0224020 A1 | 11/2004 | Schoenhard |
| 2004/0228802 A1 | 11/2004 | Chang et al. |
| 2004/0241234 A1 | 12/2004 | Vilkov |
| 2004/0253310 A1 | 12/2004 | Fischer et al. |
| 2004/0266807 A1 | 12/2004 | Oshlack et al. |
| 2005/0020613 A1 | 1/2005 | Boehm et al. |
| 2005/0031546 A1 | 2/2005 | Bartholomaus et al. |
| 2005/0063909 A1 | 3/2005 | Wright et al. |
| 2005/0106249 A1 | 5/2005 | Hwang et al. |
| 2005/0112067 A1 | 5/2005 | Kumar et al. |
| 2005/0112201 A1 | 5/2005 | Baichwal et al. |
| 2005/0118267 A1 | 6/2005 | Baichwal et al. |
| 2005/0158382 A1 | 7/2005 | Cruz et al. |
| 2005/0163717 A1 | 7/2005 | Anderson et al. |
| 2005/0186139 A1 | 8/2005 | Bartholomaus |
| 2005/0214223 A1 | 9/2005 | Bartholomaeus et al. |
| 2005/0236741 A1 | 10/2005 | Arkenau |
| 2005/0276853 A1 | 12/2005 | Baichwal et al. |
| 2006/0002860 A1 | 1/2006 | Bartholomaus |
| 2006/0018837 A1 | 1/2006 | Preston et al. |
| 2006/0039864 A1 | 2/2006 | Bartholomaus |
| 2006/0165790 A1 | 7/2006 | Walden et al. |
| 2006/0188447 A1 | 8/2006 | Arkenau-Maric |
| 2006/0193782 A1 | 8/2006 | Bartholomaus |
| 2006/0210631 A1 | 9/2006 | Patel et al. |
| 2006/0251721 A1 | 11/2006 | Cruz et al. |
| 2007/0003616 A1 | 1/2007 | Arkenau-Maric |
| 2007/0003617 A1 | 1/2007 | Fischer et al. |
| 2007/0020335 A1 | 1/2007 | Chen et al. |
| 2007/0048228 A1 | 3/2007 | Arkenau-Maric et al. |
| 2007/0110807 A1 | 5/2007 | Vergnault et al. |
| 2007/0166234 A1 | 7/2007 | Kumar et al. |
| 2007/0202167 A1 | 8/2007 | Srinivasan et al. |
| 2007/0224129 A1 | 9/2007 | Guimberteau et al. |
| 2007/0264327 A1 | 11/2007 | Kumar et al. |
| 2008/0026060 A1 | 1/2008 | Zerbe et al. |
| 2008/0044476 A1 | 2/2008 | Lyons et al. |
| 2008/0057123 A1 | 3/2008 | Grenier et al. |
| 2008/0063725 A1 | 3/2008 | Guimbertau et al. |
| 2008/0095843 A1 | 4/2008 | Nutalapati et al. |
| 2008/0107732 A1 | 5/2008 | Dharmadhikari et al. |
| 2008/0152595 A1 | 6/2008 | Emigh et al. |
| 2008/0176955 A1 | 7/2008 | Heck et al. |
| 2008/0187581 A1 | 8/2008 | Gore et al. |
| 2008/0254123 A1 | 10/2008 | Fischer et al. |
| 2008/0260815 A1 | 10/2008 | Hayes et al. |
| 2008/0260824 A1 | 10/2008 | Nangia et al. |
| 2008/0311191 A1 | 12/2008 | Nangia et al. |
| 2009/0011019 A1 | 1/2009 | Jahagirdar et al. |
| 2009/0022798 A1 | 1/2009 | Rosenberg et al. |
| 2009/0081290 A1 | 3/2009 | McKenna et al. |
| 2009/0169587 A1 | 7/2009 | Baichwal et al. |
| 2009/0214644 A1 | 8/2009 | Heasley et al. |
| 2009/0215808 A1 | 8/2009 | Yum et al. |
| 2010/0004338 A1 | 1/2010 | Sen et al. |
| 2010/0047345 A1 | 2/2010 | Crowley et al. |
| 2010/0107250 A1 | 4/2010 | Li |
| 2010/0221293 A1 | 9/2010 | Cruz et al. |
| 2010/0239662 A1 | 9/2010 | Rahmouni et al. |
| 2011/0020451 A1 | 1/2011 | Bartholomaus et al. |
| 2011/0262532 A1 | 10/2011 | Oshlack et al. |
| 2012/0107250 A1 | 5/2012 | Bartholomaus et al. |
| 2013/0209525 A1 | 8/2013 | Cruz et al. |
| 2014/0322321 A1 | 10/2014 | Herry et al. |

FOREIGN PATENT DOCUMENTS

| | | |
|---|---|---|
| EP | 0318262 A1 | 5/1989 |
| EP | 0661045 | 7/1995 |
| EP | 1293195 A1 | 3/2003 |
| EP | 1897545 | 12/2008 |
| EP | 2457563 | 5/2012 |
| EP | 2464923 | 8/2012 |
| IN | 200601004 P2 | 4/2006 |
| WO | 01/07950 | 6/1991 |
| WO | 9107950 | 6/1991 |
| WO | 95/20947 | 8/1995 |
| WO | WO-1995/020947 A1 | 8/1995 |
| WO | 97/37689 | 10/1997 |
| WO | 97/48385 | 12/1997 |
| WO | 97/49384 | 12/1997 |
| WO | 99/32120 | 7/1999 |
| WO | WO-1999-032119 A1 | 7/1999 |
| WO | 2000033835 | 6/2000 |
| WO | WO-2001/058447 A1 | 8/2001 |
| WO | 0236099 | 5/2002 |
| WO | 02/056861 | 7/2002 |
| WO | WO-2002-094254 A2 | 11/2002 |
| WO | WO-2003/015531 A2 | 2/2003 |
| WO | 2003024430 | 3/2003 |
| WO | WO-2003/026743 A2 | 4/2003 |
| WO | 2003035029 | 5/2003 |
| WO | WO-2003/092676 A1 | 11/2003 |
| WO | WO-2004/026256 A2 | 1/2004 |
| WO | WO-2004/037259 A1 | 2/2004 |
| WO | WO-2004/026283 A1 | 4/2004 |
| WO | 2005/030181 | 4/2005 |
| WO | 2005046727 | 5/2005 |
| WO | WO-2005/053587 A1 | 6/2005 |
| WO | 2006002884 | 1/2006 |
| WO | 2006124585 | 11/2006 |
| WO | 2007150074 | 12/2007 |
| WO | 2007150075 | 12/2007 |
| WO | 2008008592 | 1/2008 |
| WO | 2008115797 | 9/2008 |
| WO | 2009114606 | 9/2009 |
| WO | 2010078486 | 7/2010 |
| WO | 2010141505 | 12/2010 |
| WO | 2011/154414 | 12/2011 |
| WO | 2012092486 | 7/2012 |
| WO | 2012/112952 | 8/2012 |
| WO | 2012131463 | 10/2012 |
| WO | 2012139033 | 10/2012 |
| WO | 2013171146 | 11/2013 |

OTHER PUBLICATIONS

Written Opinion of International Searching Authority for International Application No. PCT/US14/14665 filed on Feb. 4, 2014, dated May 5, 2014, 42 pgs.

Kawashima, Y., et al., Low-Substituted Hydroxypropylcellulose as a Sustained-Drug Release Matrix Base or Disintegrant Depending on its Particle Size and Loading in Formulation, Pharmaceutical Research, vol. 10, No. 3, Mar. 1993, pp. 351-355.

Bharate, S., et al., Interactions and Incompatibilities of Pharmaceutical Excipients with Active Pharmaceutical Ingredients: A Comprehensive Review, Journal of Excipients and Food Chemistry, vol. 1, No. 3, 2010, pp. 3-26.

(56) References Cited

OTHER PUBLICATIONS

Leifert, J., et al., Acute Ischaemia of the Leg Following Accidental Intra-Arterial Injection of Dissolved Fluniltrazepam, VASA, vol. 37, No. 4, Nov. 2008, pp. 374-378.
Woodburn, K.R., et al., "Vascular Complications of Injecting Drug Misuse", British Journal of Surgery, 1996, vol. 83, p. 1329-1334.
Kim, C., "Drug Release from Compressed Hydrophilic POLYOX-WSR Tablets", Journal of Pharmaceutical Sciences, vol. 84, No. 3, Mar. 1995, p. 303-306.
Apicella, A., "Poly(ethylene oxide) (PEO) and Different Molecular Weight PEO Blends Monolithic Devices for Drug Release", Biomaterials, vol. 14, No. 2, 1993, p. 83-90.
Deighan, C.J., et al., "Rhabdomyolysis and Acute Renal Failure Resulting From Alcohol and Drug Abuse", QJ Med, vol. 93, 2000, p. 29-33.
Kalant, H., et al., "Death in Amphetamine Users: Causes and Rates", CMA Journal, vol. 112, Feb. 8, 1975, p. 299-304.
U.S. Pharmacopeia, p. 2206, 1995.
Yang, et al., "Characterization of Compressibility and Compactibility of Poly(ethylene oxide) Polymers for Modified Release Application by Compaction Simulator", Journal of Pharmaceutical Sciences, vol. 85, No. 10, Oct. 1996.
Wilkins, Jeffrey, N., "Pharmacotherapy of Schizophrenia Patients with Comorbid Substance Abuse", Schiizophrenia Bulletin, vol. 23, No. 2, 1997, http://schizophreniabulletin.oxfordjournals.org.
Moroni, et al., "Application of Poly(oxyethylene) Homopolymers in Sustained Release Solid Formulations", Drug Dev. And Indus. Pharmacy, 21(12), 1411-28 (1995).
Apicella, et al., "Poly(ethylene oxide) (PEO) Constant Release Monolithic Devices," Polymers in Medicine: Biomedical and Pharmaceutical Applications, Chapter 3 (1992).
Apicella, et al., "Poly(ethylene oxide)-Based Delivery Systems", Polymeric Drugs and Drug Administration, ACS Symposium Series 545, Chapter 9 (1994).
Zhang, F, et al., "Properties of Sustained-Release Tablets Prepared by Hot-Melt Extrusion", Pharmaceutical Development and Technology, vol. 4, No. 2, p. 241-250 (1999).
Maggi, L., et al., "Dissolution Behaviour of Hydrophilic Matrix Tablets Containing Two Different Polyethylene Oxides (PEOs) for the Controlled Release of a Water-Soluble Drug", Biomaterials, vol. 23, p. 1113-1119 (2002).
The 1997 Physician's Desk Reference ("PDR") entry for OXYCONTIN®.
Complaint for Purdue Pharma L.P., Purdue Pharmaceuticals L.P., The P.F. Laboratories, Inc., Rhodes Technologies, and *Grünenthal GMBH* v. *Ascent Pharmaceuticals, Inc.*, of U.S. Pat. No. 9,149,533, for case No. 1:18-cv-00083-RGA, dated Jan. 11, 2018, 200 pages.
Complaint for Purdue Pharma L.P., Purdue Pharmaceuticals L.P., The P.F. Laboratories, Inc., Rhodes Technologies, and *Grünenthal GMBH* v. *Ascent Pharmaceuticals, Inc.*, of U.S. Pat. No. 9,149,533, for case No. 1:18-cv-00855-RGA, dated Jun. 7, 2018, 204 pages.
Defendant Ascent Pharmaceuticals, Inc.'s answer, affirmative defenses and counterclaims to Plaintiff's complaint for case No. 1:18-cv-00083-RGA, dated Feb. 16, 2018, 30 pages.
Defendant Ascent Pharmaceuticals, Inc.'s answer, affirmative defenses and counterclaims to Plaintiff's complaint for case No. 1:18-cv-00855-RGA, dated Jun. 27, 2018, 31 pages.

* cited by examiner

TAMPER RESISTANT PHARMACEUTICAL FORMULATIONS

This application is a continuation of U.S. patent application Ser. No. 14/670,662, filed Mar. 27, 2015, which is a continuation of U.S. patent application Ser. No. 14/172,447, filed Feb. 4, 2014, which claims the benefit of U.S. Provisional Application No. 61/761,055, filed Feb. 5, 2013. The contents of which are hereby incorporated by reference in their entireties.

FIELD OF THE INVENTION

The present invention relates to the field of pharmaceutical dosage forms that are resistant to tampering and abuse.

BACKGROUND

Pharmaceutical products are sometimes the subject of abuse. For example, a particular dose of opioid agonist may be more potent when administered parenterally as compared to the same dose administered orally. Some formulations can be tampered with to provide the opioid agonist contained therein for illicit use. Opioid agonist formulations intended for oral use are sometimes crushed or subject to extraction with solvents (e.g., ethanol) by drug abusers to provide the opioid contained therein for non-prescribed illicit use (e.g., nasal or parenteral administration).

Controlled release oral dosage forms are sought out by abusers as the crushing of the dosage form may liberate an amount of active agent otherwise intended for prolonged release (e.g., 12 to 24 hours), making it immediately available. The immediate availability upon crushing may also make controlled release dosage forms more dangerous due to the possibility of accidental overdose.

Immediate release oral dosage forms are also the subject of abuse. For example, an oral dosage form may be crushed in order to make the drug therein available for administration by an unintended route, e.g., parenterally or nasally.

There have previously been attempts in the art to control the abuse potential associated with opioid analgesics. For example, the combination of pentazocine and naloxone has been utilized in tablets available in the United States, commercially available as Talwin® Nx from Sanofi-Winthrop. Talwin® Nx contains pentazocine hydrochloride equivalent to 50 mg base and naloxone hydrochloride equivalent to 0.5 mg base. Talwin® Nx is indicated for the relief of moderate to severe pain. The amount of naloxone present in this combination has low activity when taken orally, and minimally interferes with the pharmacologic action of pentazocine. However, this amount of naloxone given parenterally has profound antagonistic action to narcotic analgesics. Thus, the inclusion of naloxone is intended to curb a form of misuse of oral pentazocine which occurs when the dosage form is solubilized and injected. Therefore, this dosage has lower potential for parenteral misuse than previous oral pentazocine formulations. A fixed combination therapy comprising tilidine (50 mg) and naloxone (4 mg) has been available in Germany for the management of severe pain since 1978 (Valoron® N, Goedecke). The rationale for the combination of these drugs is effective pain relief and the prevention of tilidine addiction through naloxone-induced antagonisms at the morphine receptor. A fixed combination of buprenorphine and naloxone was introduced in 1991 in New Zealand (Temgesic® Nx, Reckitt & Colman) for the treatment of pain.

Commonly owned U.S. Patent Application Publication No. 20090081290 is directed to opioid formulations that are resistant to crushing in attempts to liberate the drug contained therein for illicit use.

Commonly owned U.S. Patent Application Publication No. 20030068375 is directed to opioid formulations that in certain embodiments include a gelling agent in an effective amount to impart a viscosity unsuitable for administration selected from the group consisting of parenteral and nasal administration to a solubilized mixture formed when the dosage form is crushed and mixed with from about 0.5 to about 10 ml of an aqueous liquid.

There exists a need in the art for a dosage form containing a drug susceptible to abuse that is resistant to oral, parenteral and nasal abuse. In the case of opioid analgesics, there exists a need for a tamper resistant formulation that does not solely rely upon the inclusion of an antagonist in the formulation to deter abuse.

All references described herein are hereby incorporated by reference in their entireties for all purposes.

OBJECTS AND SUMMARY OF THE INVENTION

It is an object of certain embodiments of the present invention to provide a solid oral dosage form comprising a drug susceptible to abuse (e.g., an opioid analgesic), which is tamper-resistant.

It is an object of certain embodiments of the present invention to provide a solid oral dosage form comprising a drug susceptible to abuse (e.g., an opioid analgesic), which is subject to less oral abuse than other dosage forms.

It is an object of certain embodiments of the present invention to provide a solid oral dosage form comprising a drug susceptible to abuse (e.g., an opioid analgesic), which is subject to less parenteral abuse than other dosage forms.

It is an object of certain embodiments of the present invention to provide a solid oral dosage form comprising a drug susceptible to abuse (e.g., an opioid analgesic), which is subject to less intranasal abuse than other dosage forms.

It is a further object of certain embodiments of the present invention to provide a solid oral dosage form comprising a drug susceptible to abuse (e.g., an opioid analgesic), which is subject to less diversion than other dosage forms.

It is a further object of certain embodiments of the present invention to provide a method of treating pain in human patients with a solid oral dosage form comprising an opioid analgesic while reducing the abuse potential of the dosage form.

It is a further object of certain embodiments of the present invention to provide a solid oral dosage form comprising a drug susceptible to abuse (e.g., an opioid analgesic), which is resistant to dose dumping in the presence of alcohol.

It is another object of certain embodiments of the present invention to treat a disease or condition (e.g., pain) by administering a solid oral dosage form as disclosed herein to a patient in need thereof.

It is another object of certain embodiments of the present invention to provide a method of manufacturing an oral dosage form of a drug susceptible to abuse (e.g., an opioid analgesic) as disclosed herein.

It is another object of certain embodiments of the present invention to provide a use of a medicament (e.g., an opioid analgesic) in the manufacture of a tamper-resistant dosage form as disclosed herein for the treatment of a disease state (e.g., pain).

The above objects of the present invention and others may be achieved by the present invention which in certain embodiments is directed to a solid oral dosage form comprising a heat-labile gelling agent; a thermal stabilizer; and a drug susceptible to abuse.

In other embodiments, the invention is directed to a solid oral dosage form comprising a heat-labile gelling agent; a thermal stabilizer; a pH-modifying agent and a drug susceptible to abuse.

In further embodiments, the invention is directed to a solid oral dosage form comprising a pH-sensitive gelling agent; a pH-modifying agent; and a drug susceptible to abuse.

In other embodiments, the invention is directed to a method of preparing the solid oral dosage forms disclosed herein, e.g., in tablet or capsule form.

In further embodiments, the present invention is directed to a method of treating a disease or condition (e.g., pain, diarrhea or constipation) comprising administering to a patient in need thereof an oral dosage form as disclosed herein.

In describing the present invention, the following terms are to be used as indicated below. As used herein, the singular forms "a," "an," and "the" include plural references unless the context clearly indicates otherwise. Thus, for example, reference to "a drug susceptible to abuse" includes a single active agent as well as a mixture of two or more different active agents, and reference to a "gelling agent" includes a single gelling agent as well as a mixture of two or more different gelling agents, and the like.

As used herein, the terms "active agent," "active ingredient," "pharmaceutical agent," and "drug" refer to any material that is intended to produce a therapeutic, prophylactic, or other intended effect, whether or not approved by a government agency for that purpose. These terms with respect to specific agents include all pharmaceutically active agents, all pharmaceutically acceptable salts thereof, and all complexes, stereoisomers, crystalline forms, cocrystals, ether, esters, hydrates and solvates thereof, and mixtures thereof, which produce the intended effect.

As used herein, the terms "therapeutically effective" refers to the amount of drug or the rate of drug administration needed to produce a desired therapeutic result.

As used herein, the terms "prophylactically effective" refers to the amount of drug or the rate of drug administration needed to produce a desired prophylactic result.

As used herein, the term "stereoisomers" is a general term for all isomers of individual molecules that differ only in the orientation of their atoms in space. It includes enantiomers and isomers of compounds with one or more chiral centers that are not mirror images of one another (diastereomers).

The term "enantiomer" or "enantiomeric" refers to a molecule that is nonsuperimposable on its mirror image and hence optically active wherein the enantiomer rotates the plane of polarized light in one direction by a certain degree, and its mirror image rotates the plane of polarized light by the same degree but in the opposite direction.

The term "chiral center" refers to a carbon atom to which four different groups are attached.

The term "patient" means a subject who has presented a clinical manifestation of a particular symptom or symptoms suggesting the need for treatment, who is treated preventatively or prophylactically for a condition, or who has been diagnosed with a condition to be treated.

"Pharmaceutically acceptable salts" include, but are not limited to, inorganic acid salts such as hydrochloride, hydrobromide, sulfate, phosphate and the like; organic acid salts such as formate, acetate, trifluoroacetate, maleate, tartrate and the like; sulfonates such as methanesulfonate, benzenesulfonate, p-toluenesulfonate and the like; amino acid salts such as arginate, asparaginate, glutamate and the like; metal salts such as sodium salt, potassium salt, cesium salt and the like; alkaline earth metals such as calcium salt, magnesium salt and the like; and organic amine salts such as triethylamine salt, pyridine salt, picoline salt, ethanolamine salt, triethanolamine salt, discyclohexylamine salt, N,N'-dibenzylethylenediamine salt and the like.

The term "subject" is inclusive of the definition of the term "patient" and does not exclude individuals who are entirely normal in all respects or with respect to a particular condition.

The term "ppm" as used herein means "parts per million". Regarding 14-hydroxycodeinone, "ppm" means parts per million of 14-hydroxycodeinone in a particular sample product. The 14-hydroxycodeinone level can be determined by any method known in the art, preferably by HPLC analysis using UV detection.

The term "heat-labile gelling agent" means a compound or composition that is capable of forming a viscous solution when combined with an aqueous liquid, but which viscosity is decreased when the viscous solution is subjected to heat.

The term "thermal stabilizer" means a compound or composition that serves to minimize or reduce the loss of viscosity that would otherwise occur when a solution of a heat-labile gelling agent is subjected to heat.

The term "pH-sensitive gelling agent" means an agent that is capable of forming a viscous solution when combined with an aqueous liquid, which viscosity is enhanced within a particular pH range.

The term "pH-modifying agent" means an agent that changes or maintains a pH within a particular pH range in an environment of use (e.g., a viscous solution obtained upon tampering of the dosage form with a liquid solvent).

The term "recovery" means the amount of drug obtained from the resultant solution of a tampered dosage form (e.g., crushing and mixing in 5 mL solvent) upon aspiration with a 27 gauge needle.

The term "tampering" means a manipulation by mechanical, thermal, and/or chemical means to obtain a solution of drug available for illicit use. The tampering can be, e.g., by means of crushing and mixing then dosage form with a solvent (with or without heat), or by dissolution of an intact dosage form in a solvent (with or without heat).

DETAILED DESCRIPTION

Immediate and controlled release dosage forms play a vital part in the management of both acute and chronic conditions (e.g., pain management with opioid analgesics). Therefore, it is important to provide a tamper-resistant dosage form of a drug susceptible to abuse that may be utilized for either controlled or immediate release to obtain a viable product that can provide effective plasma levels to a patient according to an intended release profile.

The use of gelling agents has been contemplated in order to deter the abuse of dosage forms containing a drug susceptible to abuse (e.g., an opioid analgesic). One form of abuse is via the crushing of a dosage form in order to liberate the drug contained therein for illicit use such as parenteral administration or through absorption across an external mucosal surface. When the crushed dosage form is mixed with a solution, a viscosity is obtained which inhibits the drug from being drawn into a needle, thereby hindering parenteral abuse. Similarly, when the crushed dosage form is applied to a mucosal surface (e.g., the nasal cavity), the composition forms a gel upon contact with mucosal moisture, thereby inhibiting absorption.

In order to increase the solubilization of the drug susceptible to abuse (e.g., an opioid analgesic), an abuser may heat a dosage form in an aqueous solution. This may increase the abuse potential for certain dosage forms containing gelling agents as the viscosity attained from a solubilized mixture of the dosage form may be reduced with the addition of heat, potentially facilitating parenteral or nasal administration.

Other gelling agents provide an enhanced viscosity upon solubilization when they are maintained within a particular pH range. Therefore, solubilization of these formulations outside of the particular pH range may reduce the resultant viscosity when the dosage form is solubilized.

In certain embodiments, the present invention is directed to a solid oral dosage form comprising a heat-labile gelling agent; a thermal stabilizer; a drug susceptible to abuse; and optionally a pH-modifying agent.

In other embodiments, the present invention is directed to a solid oral dosage form comprising a pH-sensitive gelling agent; a pH-modifying agent; and a drug susceptible to abuse.

In certain embodiments, the heat-labile gelling agent is a polymer such as a polysaccharide. In a particular embodiment, the polysaccharide is a microbial polysaccharide such as xanthan gum. Xanthan gum is commercially available from CP Kelco under the tradename Xantural®.

In embodiments of the present invention with xantham gum, a galactomannan (e.g., guar gum or locust bean gum) can be included to enhance the viscosity of the dosage form upon tampering with a solvent.

In other embodiments, the heat-labile gelling agent is a cellulosic material such as hydroxypropylmethylcellulose.

In certain embodiments, the thermal stabilizer can be an additional gelling agent different than the heat-labile gelling agent. In a certain embodiment, the thermal stabilizer is a pH-sensitive gelling agent. In a particular embodiment, the thermal stabilizer is a polymer, e.g., a polymer that is anionic in a neutral pH aqueous solution. In a particular embodiment, the anionic polymer is a polyacrylic acid. The polyacrylic acid can be a homopolymer, and can be optionally crosslinked with a cross-linking agent. The cross-linking agent can be a polyalcohol allyl ether such as an allyl ether pentaerythritol, an allyl ether of sucrose, an allyl ether of propylene, or a mixture thereof. Crosslinked homopolymers of acrylic acid are referred to as carbomer homopolymer and commercially available from Lubrizol under the tradename Carbopol® 71G.

In a preferred embodiment, the heat-labile gelling agent is xanthan gum and the thermal stabilizer is carbomer homopolymer.

The pH-sensitive gelling agent can also be a polymer, e.g., a polymer that is anionic in a neutral pH aqueous solution. In a particular embodiment, the pH-sensitive gelling agent is a polyacrylic acid. The polyacrylic acid can be a homopolymer and can be optionally cross-linked with a cross-linking agent (i.e, carbomer homopolymer). The cross-linking agent can be a polyalcohol allyl ether such as an allyl ether pentaerythritol, an allyl ether of sucrose, an allyl ether of propylene or a mixture thereof.

The pH-modifying agent can buffer the pH of a viscous solution obtained upon tampering of the dosage form so that it is changed to, or maintained, e.g., between about 5.5 and 8.5, between about 6 and 8, or between about 6.5 and 7.5. In certain embodiments, the pH-modifying agent can be an alkaline buffer selected from the group consisting of potassium phosphate monobasic, sodium carbonate, sodium bicarbonate, sodium chloride, sodium phosphate dibasic and sodium phosphate monobasic sodium bicarbonate. In a particular embodiment, the pH-modifying agent is sodium bicarbonate.

In a preferred embodiment, the pH-sensitive gelling agent is carbomer homopolymer and the pH-modifying agent is sodium bicarbonate.

The dosage forms of the present invention can include additional excipients in order to, e.g., aid manufacturing, provide additional tamper resistance, modify the release rate, or provide alcohol resistance.

Additional excipients may include at least one excipient selected from the group consisting of bulking agents or fillers, plasticizers, stabilizers, diluents, lubricants, disintegrants, binders, granulating aids, colorants, flavorants, and glidants.

In certain embodiments, dosage form includes a polymer that can modify the release rate of the drug contained therein. Examples of polymers that can be utilized to modify the release rate of the drug include pharmaceutically acceptable cellulosic polymers, including but not limited to cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates and mixtures thereof. Preferably, the cellulosic polymer is an alkyl cellulosic polymer such as methylcellulose or ethylcellulose.

Other release rate-modifying polymer include pharmaceutically acceptable acrylic polymers selected without limitation from acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly (methyl methacrylate) copolymer, polyacrylamide, aminoalkyl methacrylate copolymer, poly(methacrylic acid anhydride), glycidyl methacrylate copolymers, and mixtures of any of the foregoing. Preferably, the acrylic polymer is a neutral acrylic polymer (e.g., Eudragit NE 30 D®, Eudragit NE 40 D® or Eudragit NM 30 D®), which may also provide crush-resistant characteristics to the dosage form.

The drug susceptible to abuse can be dry-blended with the gelling agent(s) and any additional excipients (e.g., neutral acrylic polymer) prior to being compressed incorporation into a solid oral dosage form. In other embodiments, the materials can be wet-granulated, dried, and optionally milled prior to being incorporated into a solid oral dosage form.

In certain embodiments, a portion or all of one or more of the drug, gelling agent and any additional excipients (e.g., neutral acrylic polymer) can be incorporated extra-granularly. For example, the drug and the gelling agent(s) can be wet-granulated, dried and optionally milled. Thereafter, neutral acrylic polymer can be blended with the resultant granulation to obtain the drug-containing mixture to be compressed. Materials such as glidants and lubricants can also be added extra-granularly in order to aid in manufacturing.

A release rate-modifying polymer can be coated onto the outside of the solid oral dosage form alternatively or in addition to inclusion of the polymer within. The coating can include one or more of the release-rate modifying polymers as discussed above in an amount layered over the solid dosage form to achieve a weight gain, e.g., of from about 1% to about 30%, from about 2% to about 15%, or from about 8% to about 12% (w/w).

Individual dosage forms can also include a film coating to enhance cosmetic appearance and/or to reduce tackiness. Examples of materials to be utilized as a film coat include hydroxypropylmethylcellulose, polyvinyl alcohol, lactose, and mixtures thereof. The film coat can be: (i) an outer coating directly coated onto a dosage form (e.g., a compressed core), (ii) an outer coating directly coated onto a compressed core previously coated with a release rate-modifying coating, (iii) an intermediate layer between a compressed core and a release-rate modifying coating or (iv) a unitary coating mixed with a release rate-modifying material.

In certain embodiments, the dosage forms of the oral dosage forms of the present invention comprise from about 0.5% (w/w) to about 80% (w/w) neutral acrylic polymer, or from about 1% (w/w) to about 60% (w/w) neutral acrylic polymer, or from about 5% (w/w) to about 50% (w/w) neutral acrylic polymer, or from about 10% (w/w) to about 40% (w/w) neutral acrylic polymer.

Certain embodiments of the invention comprise a disintegrant in the formulation. The disintegrant can be an agent such as, e.g., polyvinylpyrrolidone, sodium starch glycolate, crosscarmellose sodium, or a mixture thereof.

Certain embodiments of the invention comprise a filler or diluent. The filler or diluent can be an agent such as, e.g., lactose, dextrose, mannitol, microcrystalline cellulose, or a mixture thereof.

In certain embodiments, the solid oral dosage form of the present invention comprises the heat-labile gelling agent in an amount from about 0.25% to about 75% (w/w) of the dosage form; from about 0.1% to about 25% (w/w) of the dosage form; or from about 0.5% to about 5% (w/w) of the dosage form.

In certain embodiments, the solid oral dosage form of the present invention comprises the thermal stabilizer in an amount from about 0.25% to about 90% (w/w) of the dosage form; from about 0.5% to about 50% (w/w) of the dosage form; or from about 1% to about 10% (w/w) of the dosage form.

The ratio of the heat-labile gelling agent to the thermal stabilizer can be, e.g., from about 1:10 to about 10:1 (w/w); from about 1:5 to about 5:1 (w/w); or from about 1:1 to about 1:5 (w/w).

In certain embodiments, the solid oral dosage form of the present invention comprises the pH-modifying agent in an amount from about 0.1% to about 25% (w/w) of the dosage form; from about 0.5% to about 10% (w/w) of the dosage form; or from about 1% to about 5% (w/w) of the dosage form.

In certain embodiments, the solid oral dosage form of the present invention comprises the disintegrant in an amount from about 1% to about 25% (w/w) of the dosage form; from about 4% to about 15% (w/w) of the dosage form; or from about 8% to about 12% (w/w) of the dosage form.

In certain embodiments, the solid oral dosage form of the present invention comprises the filler or diluent in an amount from about 5% to about 95% (w/w) of the dosage form; from about 25% to about 85% (w/w) of the dosage form; or from about 50% to about 75% (w/w) of the dosage form.

The ratio of the drug to the heat-labile gelling agent can be, e.g., from about 1:40 to about 40:1 (w/w); from about 1:20 to about 20:1 (w/w); from about 1:10 to about 10:1 (w/w); from about 1:5 to about 5:1 (w/w); or from about 1:3 to about 3:1 (w/w).

In addition to gelling agents, the dosage forms of the present invention can include other aversive agents to further deter the illicit use of the drug contained therein. These other aversive agents can be, e.g., an emetic, an antagonist, a bittering agent, an irritant, or a mixture thereof.

The emetic may be selected from, e.g., the group consisting of methyl cephaeline, cephaeline, emetine hydrochloride, psychotrine, O-methylpsychotrine, emetamine, ipecamine, hydro-ipecamine, ipecacunhic acid and mixtures thereof. In particular embodiments, the emetic is ipecac.

The antagonist may be selected from, e.g., the group consisting of naltrexone, naloxone, nalmefene, cyclazacine, levallorphan, pharmaceutically acceptable salts thereof, and mixtures thereof.

The bittering agent may be selected from, e.g., the group consisting of flavor oils, flavoring aromatics, oleoresins, plant extracts, leaf extracts, flower extracts, fruit extracts, sucrose derivatives, chlorosucrose derivatives, quinine sulphate, denatonium benzoate and mixtures thereof. In certain embodiments, the bittering agent is spearmint oil, peppermint oil, eucalyptus oil, oil of nutmeg, allspice, mace, oil of bitter almonds, menthol or a mixture thereof. In other embodiments, the bittering agent extracted from a fruit is selected from the group consisting of lemon, orange, lime, grapefruit, and mixtures thereof. In a particular embodiment, the bittering agent is denatonium benzoate.

The irritant may be selected from, e.g., a surfactant, capsaicin or a capsaicin analog. The capsaicin analog can be selected from the group consisting of resiniferatoxin, tinyatoxin, heptanoylisobutylamide, heptanoyl guaiacylamide, an isobutylamide, a guaiacylamide, dihydrocapsaicin, homovanillyl octylester, nonanoyl vanillylamide, and mixtures thereof.

The surfactant can be selected from the group consisting of poloxamer, a sorbitan monoester, a glyceryl monooleate, sodium lauryl sulfate and mixtures thereof.

The surfactant can be included in the dosage form in an amount, e.g., from about 1% to about 25% (w/w) of the dosage form; from about 4% to about 15% (w/w) of the dosage form; from about 2.5% to about 10% (w/w) of the dosage form or from about 8% to about 12% (w/w) of the dosage form.

The solid oral dosage forms of the present invention when mixed with from about 0.5 to about 10 ml of distilled water, provides a viscosity that prevents or reduces the ability of the drug from being drawn up into a syringe, or systemically absorbed when parenteral or nasal administration is attempted.

In certain embodiments, the viscosity provided by the solid oral dosage form after crushing and mixing with from about 0.5 to about 10 ml of distilled water or prevents or reduces the ability of the drug from being drawn up into a syringe, or systemically absorbed when parenteral or nasal administration is attempted.

In certain embodiments, the viscosity of the solid oral dosage form after crushing and mixing with from about 0.5 to about 10 ml of distilled water with heat, prevents or reduces the ability of the drug from being drawn up into a syringe, or systemically absorbed when parenteral or nasal administration is attempted.

In certain embodiments, the viscosity after tampering with from about 0.5 to about 10 ml of distilled water is at least about 10 cP, at least about 50 cP, at least about 100 cP, at least about 500 cP or at least about 1,000 cP.

In certain embodiments, the viscosity after tampering with from about 0.5 to about 10 ml of distilled water is from about 50 cP to about 1,000 cP or from about 100 cP to about 5,000 cP.

In certain embodiments, the recovery of the drug is, e.g., less than about 10%, less than about 8%, less than about 6%, less than about 4%, less than about 2%, less than about 1%, less than about 0.8%, less than about 0.6%, less than about 0.4%, or less than less than about 0.2%, based on a syringability test whereby the dosage form is mixed or crushed and mixed with 5 mL solvent and the resultant solution is aspired with a 27 gauge needle.

The solvent utilized in the syringability test can be, e.g., tap water, distilled water, sterile saline, vinegar or 40% ethanol. Also, during the syringability test, the solvent (before or after mixing with the dosage form) can be subject to heat from any source such as, e.g., by the use of a butane lighter.

In certain embodiments of the present invention, the recovery of the drug is, e.g., less than about 10%, less than about 8%, less than about 6%, less than about 4%, less than about 2%, less than about 1%, less than about 0.8%, less than about 0.6%, less than about 0.4%, or less than less than about 0.2%, based on both heated and unheated syringability tests, whereby the dosage form is mixed or crushed and mixed with 5 mL solvent and the resultant solution is aspired with a 27 gauge needle.

In certain embodiments, the ratio of extraction from an unheated stability test to a heated stability test is from about 1:5 to about 5:1; from about 1:4 to about 4:1; from about 1:3 to about 3:1; from about 1:2 to about 2:1; from about 1:1.5 to about 1.5:1; from about 1:1.3 to about 1.3:1 or from about 1:1.1 to about 1.1:1.

Active Agents

In certain embodiments, any of the following active agents can be used in the solid oral dosage form of the present invention: ACE inhibitors, adenohypophoseal hormones, adrenergic neuron blocking agents, adrenocortical steroids, inhibitors of the biosynthesis of adrenocortical steroids, alpha-adrenergic agonists, alpha-adrenergic antagonists, selective alpha-two-adrenergic agonists, analgesics, anti-pyretics, anti-inflammatory agents, androgens, local and general anesthetics, anti-addictive agents, anti-androgens, anti-arrhythmic agents, anti-asthmatic agents, anti-cholinergic agents, anti-cholinesterase agents, anti-coagulants, anti-diabetic agents, anti-diarrheal agents, anti-diuretic, anti-emetic agents, pro-kinetic agents, anti-epileptic agents, anti-estrogens, anti-fungal agents, anti-hypertensive agents, anti-microbial agents, anti-migraine agents, anti-muscarinic agents, anti-neoplastic agents, anti-parasitic agents, anti-parkinson's agents, anti-platelet agents, anti-progestins, anti-schizophrenia agents, anti-thyroid agents, anti-tussives, anti-viral agents, atypical anti-depressants, azaspirodecanediones, barbiturates, benzodiazepines, benzothiadiazides, beta-adrenergic agonists, beta-adrenergic antagonists, selective beta-one-adrenergic antagonists, selective beta-two-adrenergic agonists, bile salts, agents affecting volume and composition of body fluids, butyrophenones, agents affecting calcification, calcium channel blockers, cardiovascular drugs, cannabinoids, catecholamines and sympathomimetic drugs, cholinergic agonists, cholinesterase reactivators, contraceptive agents, dermatological agents, diphenylbutylpiperidines, diuretics, ergot alkaloids, estrogens, ganglionic blocking agents, ganglionic stimulating agents, hydantoins, agents for control of gastric acidity and treatment of peptic ulcers, hematopoietic agents, histamines, histamine antagonists, hormones, 5-hydroxytryptamine antagonists, drugs for the treatment of hyperlipoproteinemia, hypnotics, sedatives, immunosupressive agents, laxatives, methylxanthines, moncamine oxidase inhibitors, neuromuscular blocking agents, organic nitrates, opioid agonists, opioid antagonists, pancreatic enzymes, phenothiazines, progestins, prostaglandins, agents for the treatment of psychiatric disorders, psychotropics, retinoids, sodium channel blockers, agents for spasticity and acute muscle spasms, succinimides, testosterones, thioxanthines, thrombolytic agents, thyroid agents, tricyclic antidepressants, inhibitors of tubular transport of organic compounds, drugs affecting uterine motility, vasodilators, vitamins, and mixtures thereof.

In certain embodiments, the active agent is a drug susceptible to abuse (e.g., an opioid agonist). In such embodiments, the opioid agonist is selected from the group consisting of alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable salts thereof, and mixtures thereof. In certain embodiments, the opioid agonist is selected from the group consisting of codeine, fentanyl, hydromorphone, hydrocodone, oxycodone, dihydrocodeine, dihydromorphine, morphine, tramadol, oxymorphone, pharmaceutically acceptable salts thereof, and mixtures thereof.

In certain embodiments, the opioid agonist is oxycodone or pharmaceutically acceptable salts thereof in an amount, e.g., of about 2.5 mg, 5 mg, 7.5 mg, 10 mg, 15 mg, 20 mg, 25 mg or 30 mg.

In certain embodiments of the present invention, wherein the active agent is oxycodone hydrochloride, the oxycodone hydrochloride has a 14-hydroxycodeinone level of less than about 25 ppm, less than about 15 ppm, less than about 10 ppm, less than about 5 ppm, less than about 2 ppm, less than about 1 ppm, less than about 0.5 ppm or less than about 0.25 ppm.

WO 2005/097801 A1, U.S. Pat. No. 7,129,248 B2 and US 2006/0173029 A1, all of which are hereby incorporated by reference, describe a process for preparing oxycodone hydrochloride having reduced levels of 14-hydroxycodeinone.

In certain embodiments, the solid oral dosage form of the present invention comprises an active agent that is an opioid antagonist (with or without an opioid agonist). In such embodiments, the opioid antagonist is selected from the group consisting of amiphenazole, naltrexone, methylnaltrexone, naloxone, nalbuphine, nalorphine, nalorphine dinicotinate, nalmefene, nadide, levallorphan, cyclozocine, pharmaceutically acceptable salts thereof and mixtures thereof.

In certain embodiments, the solid oral dosage form of the present invention comprises an active agent that is a non-opioid analgesic. In such embodiments, the non-opioid analgesic is a non-steroidal anti-inflammatory agent selected from the group consisting of aspirin, celecoxib, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, pharmaceutically acceptable salts thereof and mixtures thereof.

In other embodiments, the present invention is directed to the dosage forms disclosed herein utilizing active agents such as benzodiazepines, barbiturates or amphetamines, their antagonists, or combinations thereof.

Benzodiazepines to be used in the present invention may be selected from alprazolam, bromazepam, chlordiazepoxide, clorazepate, diazepam, estazolam, flurazepam, halazepam, ketazolam, lorazepam, nitrazepam, oxazepam, prazepam, quazepam, temazepam, triazolam, and pharmaceutically acceptable salts, hydrates, and solvates and mixtures thereof. Benzodiazepine antagonists that can be used in the present invention include, but are not limited to, flumazenil and pharmaceutically acceptable salts, hydrates, and solvates.

Barbiturates to be used in the present invention include, but are not limited to, amobarbital, aprobarbotal, butabarbital, butalbital, methohexital, mephobarbital, metharbital, pentobarbital, phenobarbital, secobarbital and pharmaceutically acceptable salts, hydrates, and solvates mixtures thereof. Barbiturate antagonists that can be used in the present invention include, but are not limited to, amphetamines and pharmaceutically acceptable salts, hydrates, and solvates.

Stimulants to be used in the present invention include, but are not limited to, amphetamines, such as amphetamine, dextroamphetamine resin complex, dextroamphetamine, methamphetamine, methylphenidate and pharmaceutically acceptable salts, hydrates, and solvates and mixtures thereof. Stimulant antagonists that can be used in the present invention include, but are not limited to, benzodiazepines, and pharmaceutically acceptable salts, hydrates, and solvates as described herein.

Certain embodiments contain more than one active agent. For example, the dosage forms disclosed herein can contain both an opioid agonist and a non-opioid analgesic. In particular embodiments, the non-opioid analgesic is acetaminophen or a non-steroidal anti-inflammatory agent (e.g., ibuprofen, aspirin or diclofenac) and the opioid agonist is oxycodone, hydrocodone or pharmaceutically acceptable salts thereof (e.g., oxycodone hydrochloride or hydrocodone bitratrate).

The solid oral dosage forms of the present invention may comprise, e.g., from about 2.5 mg to about 10 mg oxycodone or a pharmaceutically acceptable salt thereof; from about 2.5 mg to about 15 mg hydrocodone or a pharmaceutically acceptable salt thereof; from about 325 mg to about 650 mg acetaminophen; from about 100 mg to about 800 mg ibuprofen; or from about 325 mg to about 750 mg aspirin.

Specific formulations may comprise about 2.5 mg oxycodone or a pharmaceutically acceptable salt thereof and about 325 mg acetaminophen; about 5 mg oxycodone or a pharmaceutically acceptable salt thereof and about 325 mg acetaminophen; about 7.5 mg oxycodone or a pharmaceutically acceptable salt thereof and about 325 mg acetaminophen; about 10 mg oxycodone or a pharmaceutically acceptable salt thereof and about 325 mg acetaminophen; about 7.5 mg oxycodone or a pharmaceutically acceptable salt thereof and about 500 mg acetaminophen; about 10 mg oxycodone or a pharmaceutically acceptable salt thereof and about 650 mg acetaminophen; about 5 mg oxycodone or a pharmaceutically acceptable salt thereof and about 500 mg acetaminophen; about 2.5 mg oxycodone or a pharmaceutically acceptable salt thereof and about 300 mg acetaminophen; about 5 mg oxycodone or a pharmaceutically acceptable salt thereof and about 300 mg acetaminophen; about 7.5 mg oxycodone or a pharmaceutically acceptable salt thereof and about 300 mg acetaminophen; about 10 mg oxycodone or a pharmaceutically acceptable salt thereof and about 400 mg acetaminophen; about 2.5 mg oxycodone or a pharmaceutically acceptable salt thereof and about 400 mg acetaminophen; about 5 mg oxycodone or a pharmaceutically acceptable salt thereof and about 400 mg acetaminophen; or about 7.5 mg oxycodone or a pharmaceutically acceptable salt thereof and about 400 mg acetaminophen.

Other formulations may comprise about 2.5 mg oxycodone or a pharmaceutically acceptable salt thereof and about 325 mg aspirin; about 5 mg oxycodone or a pharmaceutically acceptable salt thereof and about 325 mg aspirin; about 7.5 mg oxycodone or a pharmaceutically acceptable salt thereof and about 325 mg aspirin; about 10 mg oxycodone or a pharmaceutically acceptable salt thereof and about 325 mg aspirin; about 2.5 mg oxycodone or a pharmaceutically acceptable salt thereof and about 500 mg aspirin; about 5 mg oxycodone or a pharmaceutically acceptable salt thereof and about 500 mg aspirin; about 7.5 mg oxycodone or a pharmaceutically acceptable salt thereof and about 500 mg aspirin; about 10 mg oxycodone or a pharmaceutically acceptable salt thereof and about 500 mg aspirin In certain embodiments, the formulation comprises about 4.8355 mg oxycodone or a pharmaceutically acceptable salt thereof and 325 mg aspirin.

Further formulations may comprise about 5 mg hydrocodone or a pharmaceutically acceptable salt thereof and about 500 mg acetaminophen; about 10 mg hydrocodone or a pharmaceutically acceptable salt thereof and about 660 mg acetaminophen; about 7.5 mg hydrocodone or a pharmaceutically acceptable salt thereof and about 750 mg acetaminophen; about 5 mg hydrocodone or a pharmaceutically acceptable salt thereof and about 325 mg acetaminophen; about 7.5 mg hydrocodone or a pharmaceutically acceptable salt thereof and about 325 mg acetaminophen; about 10 mg hydrocodone or a pharmaceutically acceptable salt thereof and about 325 mg acetaminophen; about 7.5 mg hydrocodone or a pharmaceutically acceptable salt thereof and about 650 mg acetaminophen; about 10 mg hydrocodone or a pharmaceutically acceptable salt thereof and about 750 mg acetaminophen; about 10 mg hydrocodone or a pharmaceutically acceptable salt thereof and about 500 mg acetaminophen; about 5 mg hydrocodone or a pharmaceutically acceptable salt thereof and about 400 mg acetaminophen; about 7.5 mg hydrocodone or a pharmaceutically acceptable salt thereof and about 400 mg acetaminophen; about 10 mg hydrocodone or a pharmaceutically acceptable salt thereof and about 400 mg acetaminophen.

Additional formulations may comprise about 2.5 mg hydrocodone or a pharmaceutically acceptable salt thereof and about 200 mg ibuprofen; about 5 mg hydrocodone or a pharmaceutically acceptable salt thereof and about 200 mg ibuprofen; about 7.5 mg hydrocodone or a pharmaceutically acceptable salt thereof and about 200 mg ibuprofen; or about 10 mg hydrocodone or a pharmaceutically acceptable salt thereof and about 200 mg ibuprofen.

Pharmacokinetic Parameters

In certain embodiments, the formulations of the present invention comprise an opioid agonist (e.g., oxycodone hydrochloride) and provide a Tmax from about 0.5 hour to about 6 hours, or from about 1 hour to about 5 hours, or from about 2 hours to about 4 hours, or from about 2 hours to about 3 hours, or from about 1 hour to about 3 hours, or about 2.5 hours.

In certain embodiments comprising oxycodone or a pharmaceutically acceptable salt thereof (e.g., oxycodone hydrochloride), the formulation may provide a Cmax of about 30 ng/mL to about 50 ng/mL, or about 35 ng/mL to about 45 ng/mL, or about 38 to about 42 ng/mL based on a single dose of about 15 mg to a subject; or a mean Cmax of about 30 ng/mL to about 50 ng/mL, or about 35 ng/mL to about 45 ng/mL, or about 38 to about 38 ng/mL based on a single dose of about 15 mg to a population of subjects.

In other embodiments comprising oxycodone or a pharmaceutically acceptable salt thereof (e.g., oxycodone hydrochloride), the formulation may provide a Cmax of about 20 ng/mL to about 35 ng/mL, or about 22 ng/mL to about 32 ng/mL, or about 25 to about 30 ng/mL based on a single dose of about 10 mg to a subject; or a mean Cmax of about 20 ng/mL to about 35 ng/mL, or about 22 ng/mL to about 32 ng/mL, or about 25 to about 30 ng/mL based on a single dose of about 10 mg to a population of subjects.

In other embodiments comprising oxycodone or a pharmaceutically acceptable salt thereof (e.g., oxycodone hydrochloride), the formulation may provide a Cmax of about 8 ng/mL to about 20 ng/mL, or about 10 ng/mL to about 18 ng/mL, or about 12 to about 16 ng/mL based on a single dose of about 5 mg to a subject; or a mean Cmax of about 8 ng/mL to about 20 ng/mL, or about 10 ng/mL to about 18 ng/mL, or about 12 to about 16 ng/mL based on a single dose of about 5 mg to a population of subjects.

In other embodiments comprising oxycodone or a pharmaceutically acceptable salt thereof (e.g., oxycodone hydrochloride), the formulation may provide a Cmax of about 4 ng/mL to about 12 ng/mL, or about 5 ng/mL to about 10 ng/mL, or about 6 to about 8 ng/mL based on a single dose of about 2.5 mg to a subject; or a mean Cmax of about 4 ng/mL to about 12 ng/mL, or about 5 ng/mL to about 10 ng/mL, or about 6 to about 8 ng/mL based on a single dose of about 2.5 mg to a population of subjects.

In certain embodiments comprising oxycodone or a pharmaceutically acceptable salt thereof (e.g., oxycodone hydrochloride), the formulation may provide a $AUC_{0-t}$ of about 150 ng*h/mL to about 350 ng*h/mL, or about 200 ng*h/mL to about 300 ng*h/mL, or about 225 ng*h/mL to about 275 ng*h/mL based on a single dose of about 15 mg to a subject; or a mean $AUC_{0-t}$ of about 150 ng*h/mL to about 350 ng*h/mL, or about 200 ng*h/mL to about 300 ng*h/mL, or about 225 ng*h/mL to about 275 ng*h/mL based on a single dose of about 15 mg to a population of subjects.

In other embodiments comprising oxycodone or a pharmaceutically acceptable salt thereof (e.g., oxycodone hydrochloride), the formulation may provide a $AUC_{0-t}$ of about 100 ng*h/mL to about 300 ng*h/mL, or about 120 ng*h/mL to about 240 ng*h/mL, or about 150 ng*h/mL to about 200 ng*h/mL based on a single dose of about 10 mg to a subject; or a mean $AUC_{0-t}$ of about 100 ng*h/mL to about 300 ng*h/mL, or about 120 ng*h/mL to about 240 ng*h/mL, or about 150 ng*h/mL to about 200 ng*h/mL based on a single dose of about 10 mg to a population of subjects.

In other embodiments comprising oxycodone or a pharmaceutically acceptable salt thereof (e.g., oxycodone hydrochloride), the formulation may provide a $AUC_{0-t}$ of about 50 ng*h/mL to about 150 ng*h/mL, or about 60 ng*h/mL to about 120 ng*h/mL, or about 75 ng*h/mL to about 100 ng*h/mL based on a single dose of about 5 mg to a subject; or a mean $AUC_{0-t}$ of about 50 ng*h/mL to about 150 ng*h/mL, or about 60 ng*h/mL to about 120 ng*h/mL, or about 75 ng*h/mL to about 100 ng*h/mL based on a single dose of about 5 mg to a population of subjects.

In other embodiments comprising oxycodone or a pharmaceutically acceptable salt thereof (e.g., oxycodone hydrochloride), the formulation may provide an $AUC_{0-t}$ of about 20 ng*h/mL to about 100 ng*h/mL, or about 25 ng*h/mL to about 75 ng*h/mL, or about 30 ng*h/mL to about 50 ng*h/mL based on a single dose of about 2.5 mg to a subject; or a mean $AUC_{0-t}$ of about 20 ng*h/mL to about 100 ng*h/mL, or about 25 ng*h/mL to about 75 ng*h/mL, or about 30 ng*h/mL to about 50 ng*h/mL based on a single dose of about 2.5 mg to a population of subjects.

Release Rates

The solid oral dosage forms of the present invention can provide an immediate release of the active agent or a controlled release of the active agent. Certain embodiments can also provide a first portion of the active agent for immediate release and a second portion of the active agent for controlled release.

In certain embodiments, the solid oral dosage form of the present invention releases at least about 85%, at least about 90% or at least about 95% of the active agent within 45 minutes as measured by in-vitro dissolution in a USP Apparatus 2 (paddle) at 50 rpm in 500 ml Simulated Gastric Fluid (SGF) at 37° C.

In other embodiments, the solid oral dosage form of the present invention releases at least about 85%, at least about 90% or at least about 95% of the active agent within 60 minutes as measured by in-vitro dissolution in a USP Apparatus 2 (paddle) at 50 rpm in 500 ml Simulated Gastric Fluid (SGF) at 37° C.

In alternative embodiments, the solid oral dosage form of the present invention provides a dissolution release rate in-vitro of the active agent, when measured by the USP Basket Method at 100 rpm in 700 ml Simulated Gastric Fluid (SGF) without enzymes at 37° C. of at least about 15% by weight of the active agent released at 1 hour and thereafter switching to 900 ml with Phosphate Buffer at a pH of 7.5 at 37° C., of from about 25% to about 65% by weight of the active agent released at 2 hours, from about 45% to about 85% by weight of the active agent released at 4 hours, and at least about 60% by weight of the active agent released at 8 hours.

In other embodiments, the solid oral dosage form of the present invention provides a dissolution release rate in-vitro of the active agent, when measured by the USP Basket Method at 100 rpm in 700 ml Simulated Gastric Fluid (SGF) without enzymes at 37° C. for 1 hour and thereafter switching to 900 ml with Phosphate Buffer at a pH of 7.5 at 37° C., of at least about 20% by weight of the active agent released at 4 hours, from about 20% to about 65% by weight of the active agent released at 8 hours, from about 45% to about 85% by weight of the active agent released at 12 hours, and at least about 80% by weight of the active agent released at 24 hours.

Additional Excipients

The solid oral dosage forms of the present invention can include additional excipients in order to, e.g., aid manufacturing, provide additional tamper resistance, modify the release rate, or provide alcohol resistance.

The additional excipient may be at least one excipient selected from the group consisting of bulking agents, plasticizers, stabilizers, diluents, lubricants, binders, granulating aids, colorants, flavorants, and glidants.

In certain embodiments, the solid oral dosage form can include a material, e.g., a polymer that can modify the release rate of the active agent contained therein. Examples of polymers that can be utilized to modify the release of the active agent include pharmaceutically acceptable cellulosic polymers, including but not limited to cellulose esters, cellulose diesters, cellulose triesters, cellulose ethers, cellulose ester-ethers, cellulose acylates, cellulose diacylates, cellulose triacylates, cellulose acetates, cellulose diacetates, cellulose triacetates, cellulose acetate propionates, cellulose acetate butyrates and mixtures thereof. Preferably, the cellulosic polymer is an alkyl cellulosic polymer such as methylcellulose or ethylcellulose.

In other embodiments of the present invention, the release-rate modifying polymer is a pharmaceutically acceptable acrylic polymer selected without limitation from acrylic acid and methacrylic acid copolymers, methyl methacrylate copolymers, ethoxyethyl methacrylates, cyanoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), glycidyl methacrylate copolymers, and mixtures of any of the foregoing. Preferably, the acrylic polymer is a neutral acrylic polymer (e.g., Eudragit NE 30 D®, Eudragit NE 40 D® or Eudragit NM 30 D®), which can also provide crush-resistant characteristics to the dosage form.

The active agent can be dry blended with the gelling agent and the other excipients prior to being compressed into tablets or placed into a capsule. In other embodiments the materials can be wet granulated, dried and optionally milled prior to being compressed into tablets or placed into a capsule.

In certain embodiments, a portion or all of one or more of the active agent, gelling agent and additional excipient can be incorporated extra-granularly. For example, the active agent and the gelling agent can be wet granulated, dried and optionally milled. Thereafter, another excipient (e.g., thermal stabilizer) can be blended with the resultant granulation to obtain the active agent mixture. Materials such as glidants and lubricants can also be added extragranularly in order to aid in manufacturing.

A release rate-modifying material can also be coated onto a tablet or multiparticulates alternatively or in addition to inclusion of the material in the substrate. The coating can include one or more of the release modifying polymers as discussed above in an amount over the substrates to achieve a weight gain, e.g., from about 1% to about 30%, from about 2% to about 15% or from about 8% to about 12%.

Individual tablets or particles can also include a film coating to enhance cosmetic appearance and/or to reduce tackiness. Examples of materials to be utilized as a film coat include hydroxypropylmethylcellulose, polyvinyl alcohol, lactose or a mixture thereof. The film coat can be (i) an outer coating, (ii) an outer coating along with a release-modifying coating, or (iii) an intermediate layer between a substrate and a release modifying coating.

Formulations and Methods of Manufacture

The solid oral dosage forms of the present invention can be in the form of, e.g., tablets, gelcaps, capsules, caplets, granules, lozenges or bulk powders. The dosage forms of the present invention can be formulated, e.g., in a unitary form (e.g., a tablet) or a multiparticulate formulation (e.g., contained in a capsule).

When the present invention is in the form of a tablet, such tablets can be compressed, tablet triturates, enteric-coated, sugar-coated, film-coated, multiply compressed or multi-layered. The solid oral dosage forms of the present invention may provide an immediate release of the compound in the gastrointestinal tract, or alternatively may provide a controlled and/or sustained release through or at particular points in the gastrointestinal tract. The controlled and/or sustained release may be provided by, e.g., a coating on the oral dosage form or by the inclusion of the active agent in a controlled and/or sustained release matrix.

The dosage forms may optionally comprise particles containing or comprising the active agent, wherein the particles have diameter from about 0.1 mm to about 2.5 mm, preferably from about 0.5 mm to about 2 mm. Additionally, the gelling agent and/or the other excipients may be incorporated into these particles, or may be incorporated into a tablet or capsule containing these particles. In certain embodiments, the particles are film coated with a material that permits release of the active agent at a controlled rate in an environment of use. In other embodiments, the dosage forms of the present invention comprise a controlled or immediate release matrix with the active agent dispersed therein.

A unit dose of a multiparticulate dosage form of the present invention may include without limitation, from about 2 to about 75 particles; from about 10 to about 50 particles; from about 15 to about 25 particles; or from about 10 to about 50 particles. In other embodiments, a unit dose of an immediate release dosage form of the present invention may include without limitation, from about 50 to about 500 particles; from about 75 to about 350 particles; from about 100 to about 300 particles; or from about 150 to about 250 particles.

The particles of the present invention may have a mean diameter from about 0.1 mm to about 10 mm; from about 0.5 mm to about 8 mm; from about 1 mm to about 6 mm; or from about 2 mm to about 4 mm.

In certain embodiments comprising a drug, a heat-labile gelling agent and a thermal stabilizer, the dosage form can be in a matrix containing the ingredients at least partially dispersed with each other in unitary or multiparticulate form. Alternatively, the ingredients can be in laminar arrangement in either unitary or multiparticulate form.

In certain embodiments comprising a drug, a pH-sensitive gelling agent and a pH-modifying agent, the dosage form can be in a matrix containing the ingredients at least partially dispersed with each other in unitary or multiparticulate form. Alternatively, the ingredients can be in laminar arrangement in either unitary or multiparticulate form.

For example, the active agent and one or more of the excipients can be blended (with or without granulation) and compressed into a tablet. Alternatively, a granulation can be prepared which is then incorporated into a capsule. In further embodiments, an inert bead can be used as a substrate for the coating of the active agent and other excipients in single or multiple layers and placed into a capsule.

The following examples are set forth to assist in understanding the invention and should not be construed as specifically limiting the invention described and claimed herein. Such variations of the invention, including the substitution of all equivalents now known or later developed, which would be within the purview of those skilled in the art, and changes in formulation or minor changes in experimental design, are to be considered to fall within the scope of the invention incorporated herein.

EXAMPLES

Examples 1A-E

In Examples 1A-1E, immediate release oxycodone hydrochloride tablets with abuse deterrent properties were prepared in accordance with Table 1.

TABLE 1

| Component and Grade | Function | Ex. 1A 5 mg | Ex. 1B 10 mg | Ex. 1C 15 mg | Ex. 1D 20 mg | Ex. 1E 30 mg |
|---|---|---|---|---|---|---|
| Oxycodone HCl, USP | API | 5 (1.25) | 10 (2.5) | 15 (3.75) | 20 (5) | 30 (7.5) |
| Sodium Lauryl Sulfate, NF | Irritant | 40 (10) | 40 (10) | 40 (10) | 40 (10) | 40 (10) |
| Magnesium Stearate, NF | Lubricant | 4 (1) | 4 (1) | 4 (1) | 4 (1) | 4 (1) |
| Xanthan Gum, NF (Xantural 75) | Gelling Agent | 6 (1.5) | 6 (1.5) | 6 (1.5) | 6 (1.5) | 6 (1.5) |
| Carbomer Homopolymer Type A, NF (Carbopol ® 71G NF Polymer) | Gelling Agent | 20 (5) 10 (2.5) | 20 (5) 10 (2.5) | 20 (5) 10 (2.5) | 20 (5) 10 (2.5) | 20 (5) 10 (2.5) |
| Sodium Bicarbonate, USP | pH Neutralizer | | | | | |
| Crospovidone NF (Polyplasdone XL-10) | Disintegrant | 36 (9) | 36 (9) | 36 (9) | 36 (9) | 36 (9) |
| Microcrystalline Cellulose, NF (Avicel PH102) | Filler | 279 (69.75) | 274 (68.5) | 269 (67.25) | 264 (66.0) | 254 (63.5) |

Manufacturing Procedure
(i) Half of the microcrystalline cellulose was added into a V-blender.
(ii) The remaining ingredients, except the magnesium stearate, were added to the blender with the oxycodone HCl passed through a 30 mesh screen to delump.
(iii) The mixture was allowed to blend for 5 minutes.
(iv) The magnesium stearate was added, and mixed for an additional minute.
(v) The blend was discharged and compressed on a Kilian Rotary Tablet Press using caplet shaped tooling, (0.650×0.292 inches) to a target hardness of 7 Kp and a thickness of about 4.7 mm.

Examples 2A-D

Syringability Testing Procedure

A single tablet of each of Examples 2A-E set forth in Table 2 was crushed using a 4 oz. mortar and pestle for 1 minute. The crushed tablet was transferred to a scintillation vial. A timer was set for 5 minutes. Using a 5 mL syringe, 5 mL of solvent was added to the scintillation vial, the timer was started, and the vial was shaken for 30 seconds. This solution was poured into a small weighing dish. A small pea-size piece of cotton was placed in the weighing dish with the solution, and aspiration was attempted, using a 5 mL syringe with a 27 gauge needle, until the timer signaled to stop. The aspirated solution was transferred to a 25 mL volumetric flask, which was diluted with proper mobile phase used for analysis of oxycodone HCl.

Testing the syringability on heated samples was performed in the same manner, except that after the solvent was added, a butane lighter was used to heat the vial until the liquid started to bubble. Then the remainder of the procedure was followed, with attempting to aspirate for 5 minutes.

TABLE 2

| Ingredient | Ex. 2A | Ex. 2B | Ex. 2C | Ex. 2D |
|---|---|---|---|---|
| Oxycodone HCl | 30 mg | 5 mg | 5 mg | 30 mg |
| MCC | 262 mg | 275 mg | 275 mg | 250 mg |
| Sodium Lauryl Sulfate, NF | 40 mg | 40 mg | 40 mg | 40 mg |
| Crospovidone NF | 40 mg | 40 mg | 40 mg | 40 mg |
| Xanthan Gum, NF | 6 mg | 6 mg | 6 mg | 6 mg |
| Carbomer Homopolymer Type A, NF | 12 mg | 20 mg | 20 mg | 20 mg |
| Sodium Bicarbonate, USP [Grade 1] | 6 mg | 10 mg | 10 mg | 10 mg |
| Magnesium Stearate, NF | 4 mg | 4 mg | 4 mg | 4 mg |

In Tables 3 and 4, the data is depicted for tablets from the examples of Table 2 which were tested for syringability at room temperature (unheated), and heated as disclosed in the syringability procedure. To simulate real world situations, various solvents were used. All samples were tested in duplicate.

TABLE 3

Unheated Sample Results

| Solvent | Ex. A, B, C or D | Volume Aspirated (mL) | Oxycodone Recovered (mg) | % Oxycodone Recovered |
|---|---|---|---|---|
| Tap Water | C | 0.05 | 0.0249 | 0.5 |
| | | 0.05 | 0.0845 | 1.69 |
| | D | 0.05 | 0.2906 | 0.97 |
| | | 0 | 0 | 0 |
| Distilled Water | A | 0.2 | 2.0 | 6.0 |
| | | 0.4 | 2.0 | 8.0 |
| Sterile Saline | B | 0.05 | 0.0262 | 0.5 |
| | | 0.2 | 0.0951 | 1.9 |
| Vinegar | B | 0.3 | 0.3222 | 6.4 |
| | | 0.3 | 0.2722 | 5.4 |
| 40% Ethanol | B | 0.2 | 0.1912 | 3.8 |
| | | 0.3 | 0.2988 | 6.0 |

TABLE 4

Heated Sample Results

| Solvent | Ex. A, B, C or D | Volume Aspirated (mL) | Oxycodone Recovered (mg) | % Oxycodone Recovered |
|---|---|---|---|---|
| Tap Water | C | 0.05 | 0.0203 | 0.4 |
| | | 0.05 | 0.0097 | 0.2 |
| | D | 0.05 | 0.282 | 0.94 |
| | | 0.05 | 0.5237 | 1.75 |
| Distilled Water | A | 0.4 | 2.5 | 8.0 |
| | | 0.5 | 3.2 | 11.0 |
| Sterile Saline | B | 0.05 | 0.0282 | 0.6 |
| | | 0.2 | 0.1145 | 2.29 |
| Vinegar | B | 0.3 | 0.353 | 7.1 |
| | | 0.4 | 0.4155 | 8.31 |
| 40% Ethanol | B | 0.3 | 0.3619 | 7.2 |
| | | 0.3 | 0.2585 | 5.2 |

The above data shows that the gelling agents are effective to inhibit aspiration by small volume extraction with various solvents both at room temperature and after the sample is heated to boiling temperature.

We claim:

1. A solid oral dosage form comprising
a heat-labile gelling agent;
a thermal stabilizer comprising an anionic polymer in a neutral pH aqueous solution; and
a drug susceptible to abuse,
wherein the solid oral dosage form releases at least about 85% of the drug susceptible to abuse within 45 minutes as measured by in-vitro dissolution in a USP Apparatus 2 (paddle) at 50 rpm in 500 ml SGF at 37° C.

2. The solid oral dosage form of claim 1, wherein the polysaccharide is a microbial polysaccharide.

3. The solid oral dosage form of claim 2, wherein the microbial polysaccharide is xanthan gum.

4. The solid oral dosage form of claim 1, further comprising a pH-modifying agent.

5. The solid oral dosage form of claim 4, wherein the pH-modifying agent provides a pH of between about 5.5 and 8.5 to a viscous solution obtained when the dosage form is crushed and mixed with 5 mL of distilled water.

6. The solid oral dosage form of claim 1, further comprising a disintegrant.

7. The solid oral dosage form of claim 1, further comprising a filler.

8. The solid oral dosage form of claim 7, wherein the filler is selected from the group consisting of lactose, dextrose, mannitol, microcrystalline cellulose and a mixture thereof.

9. The solid oral dosage form of claim 1, comprising the heat-labile gelling agent in an amount from 0.25% to about 75% (w/w) of the dosage form.

10. The solid oral dosage form of claim 1, comprising the thermal stabilizer in an amount from about 0.25% to about 90% (w/w) of the dosage form.

11. The solid oral dosage form of claim 1, further comprising an aversive agent.

12. The solid oral dosage form of claim 11, wherein the aversive agent is a surfactant, capsaicin or a capsaicin analog.

13. The solid oral dosage form of claim 1, wherein the drug is an opioid agonist.

14. The solid oral dosage form of claim 13, wherein the opioid agonist is selected from the group consisting of codeine, morphine, oxycodone, oxymorphone, hydrocodone, hydromorphone, pharmaceutically acceptable salts thereof, and mixtures thereof.

* * * * *